United States Patent
Uchino et al.

(10) Patent No.: US 6,291,738 B1
(45) Date of Patent: Sep. 18, 2001

(54) OUTFIT SUPPORTING MEMBER AND OUTFIT MADE BY USING THE SAME

(75) Inventors: Hiroyuki Uchino; Yoshikazu Izumihara; Hiroshi Maki, all of Kawasaki; Naomitsu Takekawa, Itabashi-ku; Yukihiro Katoh, Funabashi; Akihito Watanabe, Sakai-gun, all of (JP)

(73) Assignees: Alcare Co., Ltd., Tokyo; Sakase Adtech Co., Ltd., Fukui; Maki Hirosi, Kanagawa, all of (JP)

( * ) Notice: Subject to any disclaimer, the term of this patent is extended or adjusted under 35 U.S.C. 154(b) by 0 days.

(21) Appl. No.: 09/230,921

(22) PCT Filed: Jun. 3, 1998

(86) PCT No.: PCT/JP98/02447

§ 371 Date: Sep. 28, 2000

§ 102(e) Date: Sep. 28, 2000

(87) PCT Pub. No.: WO98/55160

PCT Pub. Date: Dec. 10, 1998

(30) Foreign Application Priority Data

Jun. 3, 1997 (JP) .................................................. 9-145290

(51) Int. Cl.$^7$ .................................................. A61F 13/00

(52) U.S. Cl. .......................................... 602/42; 139/387 R

(58) Field of Search ........................... 602/42; 139/387 R, 139/421

(56) References Cited

U.S. PATENT DOCUMENTS 4,340,091 * 7/1982 Skelton et al. .

* cited by examiner

Primary Examiner—Michael A. Brown
Assistant Examiner—Lalita M. Hamilton
(74) Attorney, Agent, or Firm—Wenderoth, Lind & Ponack, L.L.P.

(57) ABSTRACT

This invention provides holding and supporting appliances used in the fields of orthopedics, rehabilitation and sports and support members thereof that are light in weight, thin, rigid and durable and breathe well, and, furthermore, support members made of reinforced plastic triaxial woven fabrics impregnated with resin. The support members according to this invention include a piece formed of reinforced plastic triaxial woven fabrics. Preferably, the formed piece should have openings representing 5 to 33 percent of the overall area thereof, and a flexural rigidity of 10 to $1 \times 10^4$ kg·mm$^2$ per unit width and a basis weight (weight per unit area) of 50 to 1000 g/m$^2$. Holding and supporting appliances are formed by using the support members described above.

3 Claims, 1 Drawing Sheet

OUTFIT SUPPORTING MEMBER AND OUTFIT MADE BY USING THE SAME

FIELD OF THE INVENTION

This invention relates to mask-like support members suited for use with braces, and more particularly to appliances to support or fasten bodily parts and support members formed of plastics reinforced with triaxial woven fabrics suited for use with artificial limbs and other such appliances.
Background of the Invention Brace support members are used with supporters, braces, rehabilitation appliances and artificial limbs that are intended to reduce loads acting on bones, joints and muscles or fasten them in position by supporting or fastening limbs or the trunk of the human body. Brace support members are generally made by combining foamed resin sheets, cloth or other similar materials so as to keep out of direct contact with skins and provide better fitting with the shape and motion of bodies.

Conventional brace support members have mostly been made by forming such thermoplastic plastics as polyethylene, polypropylene, polycarbonate and nylon.

Because brace support members are required to have high rigidity and durability, those made of plastics with low strengths and low moduli of elasticity are used by imparting the required rigidity and durability by increasing thickness.

Increasing the thickness to provide the necessary rigidity and durability to the braces made of conventional used plastics results in increased weight. In addition, plastics tend to cause sweating, stuffiness, unsanitary conditions, itching and other unwelcome problems because they do not breathe. Provision of openings to permit ventilation entails lowering of rigidity and durability which, in turn, necessitates further increase of thickness to insured the required rigidity and durability. Reinforced plastic unidirectional or biaxial woven fabrics are lighter and more rigid than unreinforced ones. Even so, such reinforced plastic fabrics also undergo unavoidable lowering of rigidity and durability when ventilating openings are provided. Summary of the Invention The object of this invention is to provide holding and supporting appliances used in the fields of orthopedics, rehabilitation and sports and support members thereof that are light in weight, thin, rigid and durable and permeability well, and, furthermore, to provide support members made of reinforced plastic triaxial woven fabrics impregnated with resin.

To achieve the above object, the support members according to this invention comprises a mask-like piece formed of reinforced plastic triaxial woven fabrics.

Preferably, the formed piece should have openings representing 5 to 33 percent of the overall area thereof, and a flexural rigidity of 10 to $1 \times 10^4$ kg·mm² per unit width in at least one direction and a basis weight (weight per unit area) of 50 to 1000 g/m².

Holding and supporting appliances are formed by using the support members described above.

BRIEF DESCRIPTION OF THE DRAWINGS

In FIG. 1, reference numerals 1 and 2 designate a bundle of fibers impregnated with resin and an opening provided in the fabric respectively.

DESCRIPTION OF THE PREFERRED EMBODIMENTS

Figure 1A:
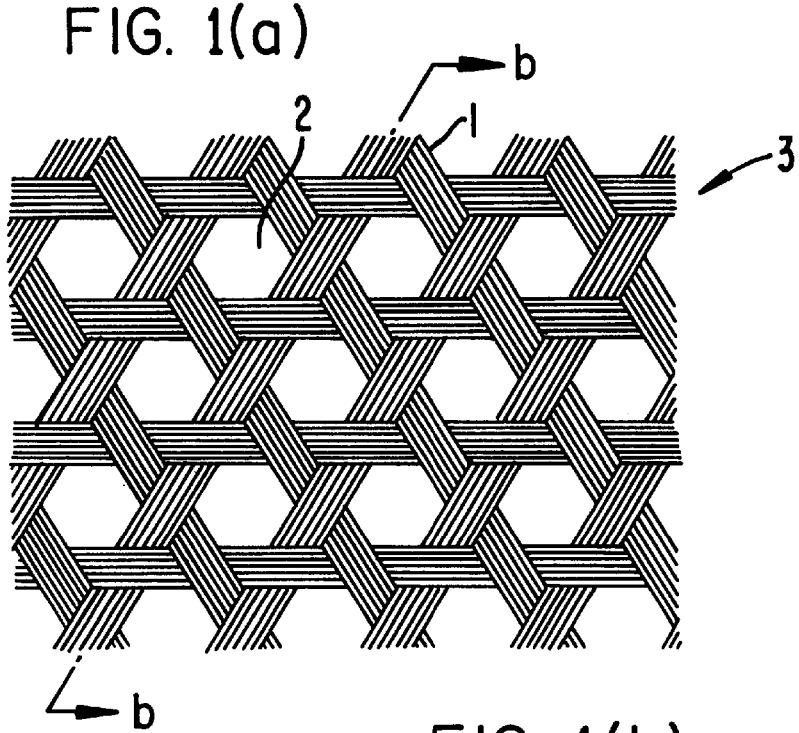
FIG. 1 schematically illustrates a triaxial woven fabric used in this invention: (a) is a plan view of a plastic-reinforced triaxial woven fabric impregnated with resin; and (b) is a cross-sectional view taken along line b—b of the fabric shown in (a).
Figure 1B:

A mask-like piece made by forming plastic-reinforced triaxial woven fabric is obtained by laminating two or more sheets of plastic-reinforced triaxial woven fabric of carbon or glass fibers that are impregnated with resin after being woven or of triaxial woven fabric of reinforced fibers pre-impregnated with resin.

The reinforced plastic triaxial woven fabrics according to this invention are made of inorganic fibers, such as carbon, glass and metal fibers, and organic fibers, such as aramid and polyethylene fibers having high moduli of elasticity, or combinations of two or more of them. Of these, carbon fibers are particularly suited to this purpose because they are highly elastic fibers with low specific gravity capable of obtaining the same rigidity with lighter weight.

The resins impregnating to the triaxial woven fabrics is able to use various types of known thermosetting or thermoplastic resins. Such thermosetting resins include epoxy, unsaturated polyester, vinyl-ester and polyurethane resins, whereas such thermoplastic resins include polyamide, polyester and polycarbonate resins. Choice must be made by considering the method of manufacturing and forming reinforced plastic triaxial woven fabrics and their uses. For example, thermosetting resins with low viscosity are suited for impregnating triaxially woven fabrics, whereas flexible thermoplastic resins are suited for weaving reinforced plastic threads into triaxial woven fabrics.

Reinforced plastic triaxial woven fibers are formed into brace support members according to this invention by known forming methods used with reinforced plastic fabrics. One method, for example, comprises impregnating a triaxial woven fabric, placing the impregnated fabric in a mold of metal or wood, and forming into a desired shape by applying pressure and heat, with subsequent cooling. Another method weaves bundles of fibers pre-impregnated with resin into a triaxial woven fabric and forms the fabric into a desired shape by using a metal mold or other similar device.

Formed pieces of reinforced plastic triaxial woven fabrics according to this invention should have openings representing 5 to 33 percent of the overall area thereof. If the area of openings is smaller, adequate permeability will not be obtained. Then, such formed pieces cause sweating, stuffiness, unsanitary conditions, itching and other unwelcome problems. Theoretically, the total area of openings in a triaxially woven fabric can not exceed the upper limit of 33 percent.

The flexural rigidity per unit width in at least one direction is between 10 to $1 \times 10^4$ kg·mm². If the flexural rigidity is lower than 10 kg·mm², brace support members cannot effectively support or hold the human body. If, on the other hand, the flexural rigidity is higher than $1 \times 10^4$ $kg\text{-}mm2$, then brace support members may bite into the human body and may not permit continued use because of pain. Here, the flexural rigidity per unit width means the flexural rigidity divided by the width of the specimen. The flexural rigidity per unit width need not be uniform in all directions of the brace support member. The flexural rigidity per unit may be varied as required by individual bodily parts and uses, as by increasing in the direction or part where strong constraint is necessary and decreasing in the direction or part where a profile fitting well with the human body is required.

Locally varied flexural rigidity can be obtained by making a triaxial woven fabric by using fibers having three different moduli of elasticity in three directions or by putting one fabric over another in desired areas. The basis weight on the brace support members must be 50 to 1000 g/m$^2$. If the basis weight is lighter than 50 g/m$^2$, it is difficult to obtain the desired rigidity and openings of the desired area. If the weight is heavier than 1000 g/m$^2$, brace support members themselves will become too heavy to permit easy walk or other bodily movements and continued use over a long period of time. This reduces the effectiveness of he brace support members in medical treatment.

The flexural rigidity per unit width and the basis weight within the specified ranges of this invention can be obtained by defining the modulus of elasticity of the fibers, the number of the fibers in each bundle, openings in the fabric (the clearance between the bundles of the fibers making up the fabric), the thickness of the fabric, the number of and clearance between the sheets to be placed one on top of the other, and the area of the parts where the sheets are placed one on top of the other.

The brace support members of this invention are used in conjunction with foamed resin sheets, cloth or other similar materials so as to keep out of direct contact with skins and provide better fitting with the shape and motion of bodies, as with conventional ones made by forming unreinforced plastics. To insure good permeability, it is preferable to use open-cell resin sheets, non-woven fabrics, loosely woven fabrics and clothes readily absorbing sweats from the skin, or combinations thereof. It is also preferable to cover the edges of plastic-reinforced triaxially woven fibers with soft and flexible resin to prevent injuries to the human body.

EXAMPLE 1

Bundles comprising 6000 threads of a carbon fiber having a tensile strength of 360 kgf/mm$^2$ and a tensile modulus of elasticity of 23500 kgf/mm$^2$ were woven into a triaxial fabric (1) with a weaving density (the number of fiber bundles per 10 cm of fabric) of 18.2. The triaxial fabric (1) had 33 percent of openings (2) therein. The triaxial fabric (1) was impregnated with a mixture of 100 parts by weight of epoxy resin (the Epikote 828 prepared by Yuka Shell Epoxy Co., Ltd.), 3 parts by weight of hardener (boron trifluoride monoethylamine) and 150 parts by weight of 3-butanone as a solvent, and then formed into a prepreg (3) after drying in the air for 8 hours. The prepreg (3) was curved and fastened along the periphery of a cylindrical wooden mold having a diameter of 150 mm. The curved prepreg was allowed to harden for 1 hour in a hot oven kept at 130° C., cooled, and cut into a formed piece (4) of reinforced plastic triaxial woven fiber 300 mm long in the circumferential direction and 150 mm in the axial direction of the cylinder. The formed piece (4) had a thickness of 0.9 mm and a weight of 31 g, with a basis weight of 690 g/m$^2$ and openings (2) accounting for 30 percent of the overall area thereof.

To determine the flexural rigidity per unit width of the formed piece, the prepreg (3) was placed between two sheets of aluminum, allowed to harden for 1 hour in a hot oven kept at 130° C., cooled, and then cut into a 300 mm square flat sheet of reinforced plastic triaxial woven fabric. This sheet proved to have a flexural rigidity of 82 kgf/mm$^2$ per unit width.

EXAMPLE 2

Bundles comprising 3000 threads of a carbon fiber having a tensile strength of 345 kgf/mm$^2$ and a tensile modulus of elasticity of 35000 kgf/mm$^2$ were woven into a triaxial fabric (1) with a weaving density (the number of fiber bundles per 10 cm of fabric) of 36.4. The triaxial fabric (1) had 33 percent of openings (2) therein. A prepreg (3) was prepared as in the case of Example 1 and then cut into a formed piece (4) of reinforced plastic triaxial woven fabric of the same shape as the one in Example 1. The formed piece (4) had a thickness of 0.4 mm and a weight of 15 g, with a basis weight of 330 g/m$^2$ and openings (2) accounting for 25 percent of the overall area thereof.

A flat sheet of the reinforced plastic triaxial woven fabric was prepared from the prepreg (3), as in the case of Example 1. The sheet proved to have a flexural rigidity of 13 kgf/mm$^2$ per unit width.

EXAMPLE 3

Two prepregs (3) prepared in Example 2 were placed one on top of the other, with the openings (2) in the two prepregs aligned with each other, and then cut into a formed piece (4) of the reinforced plastic triaxial woven fiber of the same shape as the one in Example 1. The formed piece (4) had a thickness of 0.7 mm and a weight of 31 g, with a basis unit of 650 g/m$^2$ and openings (2) accounting for 19 percent of the overall area thereof.

A two-layered flat sheet of the reinforced plastic triaxial woven fabric was prepared from the prepreg (3), as in the case of Example 1. The sheet proved to have a flexural rigidity of 100 kgf/mm$^2$ per unit width.

EXAMPLE 4

Bundles comprising 3000 threads of a carbon fiber having a tensile strength of 375 kgf/rmM$^2$ and a tensile modulus of elasticity of 50000 kgf/mm$^2$ were woven into a triaxial fabric (1) with a weaving density of 36.4. The triaxial fabric (1) had 33 percent of openings (2) therein. A prepreg (3) was prepared as in the case of Example 1. A three-layered formed piece (4) of the reinforced plastic triaxial woven fabric was prepared from the prepreg (3), as in the case of Example 1. The formed piece (4) had a thickness of 1.9 mm and a weight of 45 g, with a basis unit of 980 g/m$^2$ and openings (2) accounting for 14 percent of the overall area thereof.

A flat sheet of the reinforced plastic triaxial woven fabric was prepared from the prepreg (3), as in the case of Example 1. The sheet proved to have a flexural rigidity of 2500 kgf/mm$^2$ per unit width.

Example for Comparison 1

A 3 mm thick sheet of high-density polyethylene having a tensile strength of 4.5 kgf/mm$^2$ and a tensile modulus of elasticity of 56 kgf/mm$^2$ was heated to 190° C. using an infrared heater. The heated sheet was curved along a cylindrical wooden mold having a diameter of 150 mm, allowed to solidify by cooling, and cut into a formed piece of non-reinforced plastic 300 mm long in the circumferential direction and 150 mm in the axial direction of the cylinder. The formed piece had a thickness of 2.8 mm and a weight of 118 g, with a basis weight of 2630 g/m$^2$.

The high-density polyethylene heated to 190° C. using an infrared heater was placed between two sheets of aluminum, allowed to solidify by cooling, and cut into 300 mm square sheet. The sheet had a thickness of 2.8 mm and a flexural rigidity of 103 kgf/mm$^2$.

Example for Comparison 2

A 1 mm thick sheet of high-density polyethylene having a tensile strength of 4.5 kgf/mm$^2$ and a tensile modulus of elasticity of 56 kgf/mm² was heated to 190° C using an infrared heater. The heated sheet was curved along a cylindrical wooden mold having a diameter of 150 mm, allowed to solidify by cooling, and cut into a formed piece of non-reinforced plastic 300 mm long in the circumferential direction and 150 mm in the axial direction of the cylinder. The formed piece had a thickness of 0.9 mm and a weight of 39 g, with a basis weight of 875 g/m².

The high-density polyethylene heated to 190° C. using an infrared heater was placed between two sheets of aluminum, allowed to solidify by cooling, and cut into 300 mm square sheet (18). The sheet had a thickness of 0.9 mm and a flexural rigidity of 8 kgf/mm².

Example for Comparison 3

Five prepregs (3) prepared in Example 1 were placed one on top of the other, with the openings in the five prepregs aligned with each other, and then cut into a formed piece of the reinforced plastic triaxial woven fiber of the same shape as the one in Example 1. The formed piece had a thickness of 4.9 mm and a weight of 153 g, with a resin impregnation of 3400 g/m² and openings accounting for 12 percent of the overall area thereof.

33 percent of the overall area. All of them proved to have good levels of fitness and supporting strength. The prototype made from the formed piece of Example 2 exhibited a good level of fitness but a somewhat smaller restraining force than those made from the formed pieces of Examples 1, 3 and 4, though the difference was practically negligible.

By comparison, the one made from the formed piece of Example for Comparison 1 was so heavy, because of the heavier basis weight, that it dragged down, required re-fitting, and, therefore, proved inconvenient for practical use. The one made from the formed piece of Example for Comparison 2 was low in rigidity, had a too small restraining force, and, as such, proved unsuitable for practical use. The one made from the formed piece of Example for Comparison 3 was too rigid to permit smooth following of the motion of thigh, bit into the body, and thus made it difficult to continue walking for periods longer than 10 minutes. Precluding breathing, in addition, the prototypes made from the formed pieces of Examples for Comparison 1 to 3 caused stuffiness due to sweating that, in turn, led to unpleasantness.

TABLE 1

| Semicylindrical formed piece | Formed Piece | Example 1 Formed piece (3) | Example 2 Formed Piece (7) | Example 3 Formed Piece (9) | Example 4 Formed Piece (13) | Example for Comparison 1 Formed Piece (15) | Example for Comparison 2 Formed Piece (17) | Example for Comparison 3 Formed Piece (19) |
|---|---|---|---|---|---|---|---|---|
| | Material | Triaxially woven fabric | Triaxially woven fabric | Triaxially woven fabric | Triaxially woven fabric | Superhigh polymeric polyethylene | Superhigh polymeric polyethylene | Triaxially woven fabric |
| | Thickness (mm) | 0.9 | 0.4 | 0.7 | 1.9 | 2.8 | 0.9 | 4.9 |
| | Weight (g) | 31 | 15 | 31 | 45 | 118 | 39 | 153 |
| | Basis weight (g/m²) | 690 | 330 | 650 | 980 | 2630 | 875 | 3400 |
| | Flexural Rigidity per Unit Width (kgf · mm²) | 82 | 13 | 100 | 2500 | 103 | 8 | $1.3 \times 10^4$ |
| Brace prototype | Fitness | Good | Good | Good | Good | Heavy, drag-down, stuffiness due to sweating | Stuffiness due to sweating | Biting into body, stuffiness due to sweating |
| | Support | Good | Fair | Good | Good | Good | Lack of rest | Good |
| Evaluation of support | | ◎ | ○ | ◎ | ◎ | X | X | X |

A five-layered flat sheet of the plastic-reinforced triaxially woven fabric was prepared from the prepreg (3), as in the case of Example 1. The sheet proved to have a flexural rigidity of $1.3 \times 10^4$ kgf/mm² per unit width.

Figure 2:
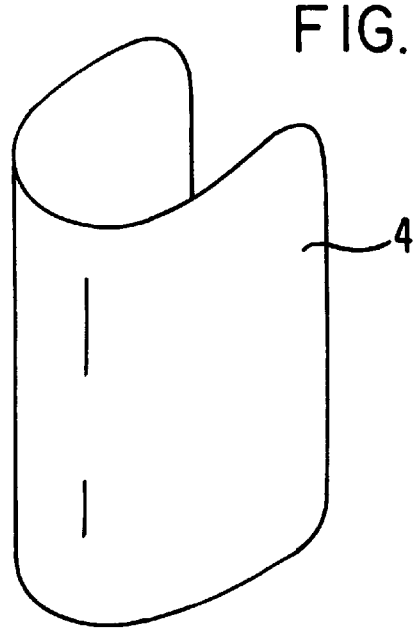
FIG. 2 schematically shows a knee joint brace according to this invention used in the treatment of osteoarthritis of the knee.

The semicylindrical formed pieces prepared in Examples 1 to 4 and Examples for Comparison 1 to 3 were made into support members by cutting off the four corners thereof with a radius of approximately 50 mm. Each support member was formed into a prototype of brace to support the knee joint used in the care of osteoarthritis of the knee by fastening with two rubber bands, as shown in FIG. 2.

Table 1 shows the degrees of fitness evaluated by persons who walked for an hour with the prototype mounted on their thighs.

The prototypes made from the formed pieces prepared in Examples 1 to 4 had a flexural rigidity of 10 to $1 \times 10^4$ kg mm² per unit width of corresponding flat sheets, a basis weight of 50 to 1000 g/m², and openings representing 5 to Industrial Applicability This invention provides brace support members made by forming light permeable reinforced plastic triaxial woven fabrics. The brace support members according to this invention have sanitary and industrial advantages because they are light and good to put on, cause less stuffiness due to sweating, and permit comfortable continuous wearing.

What is claimed is:

1. A brace support member comprising a formed piece of reinforced plastic triaxial woven fabric having openings representing 5 to 33 percent of the overall area thereof, a flexural rigidity of 10 to $1 \times 10^4$ kg.mm per unit width, at least in one direction thereof, and a basis weight (weight per unit area) of 50 to 1000 g/m².

2. A brace made by using the brace support member according to claim 1.

3. A brace according to claim 2, wherein the edges of the brace support member are covered with soft and flexible resin.

\* \* \* \* \*